US005623086A

United States Patent [19]
Perri et al.

[11] Patent Number: 5,623,086
[45] Date of Patent: Apr. 22, 1997

[54] PROCESS FOR THE PRODUCTION OF 1,2-BIS (ACYLOXYLATES)

[75] Inventors: Steven T. Perri; Stephen N. Falling, both of Kingsport, Tenn.

[73] Assignee: Eastman Chemical Company, Kingsport, Tenn.

[21] Appl. No.: 581,704

[22] Filed: Dec. 29, 1995

[51] Int. Cl.$^6$ .................................................. C07C 67/24
[52] U.S. Cl. ............................................ 560/240; 560/112
[58] Field of Search ....................................... 560/240, 112

[56] References Cited

U.S. PATENT DOCUMENTS 5,189,199  2/1993  Godleski .................................. 560/93

OTHER PUBLICATIONS

Paust, J., *Pure and Appl. Chem.*, 63, p. 45 (1991).
Shvets, V. F., et al., *Kinet. Katal.*, 16(3), pp. 785–788 (1975).
Shvets, V. F., et al., *Kinet Katal.*, 16(2), pp. 425–430 (1975).
Swindell, C. S., et al., *J. Org. Chem.*, 55, p. 3 (1990).
Fraser–Reid, B., et al., *J. Amer. Chem. Soc.*, 107, p. 5576 (1985).
Evans, R. M., et al., *J. Chem Soc.*, p. 248 (1949).
Ali, S., et al., *J. Org. Chem.*, 53, p. 5547, (1988).

*Primary Examiner*—Michael L. Shippen
*Attorney, Agent, or Firm*—Cheryl J. Tubach; Harry J. Gwinnell

[57] ABSTRACT

A process for the preparation of 1,2-bis(acyloxyates) comprises acylation of epoxides with carboxylic anhydrides in the presence of a catalytic composition containing a tertiary amine and a carboxylic acid. Preferably, the carboxylic acid is a conjugate acid of the carboxylic anhydride. The carboxylic acid acts as a co-catalyst and its use in conjunction with the tertiary amine significantly increases the rate of reaction and results in higher selectivity. The catalytic composition may be prepared prior to acylation or in situ providing application versatility.

19 Claims, 1 Drawing Sheet

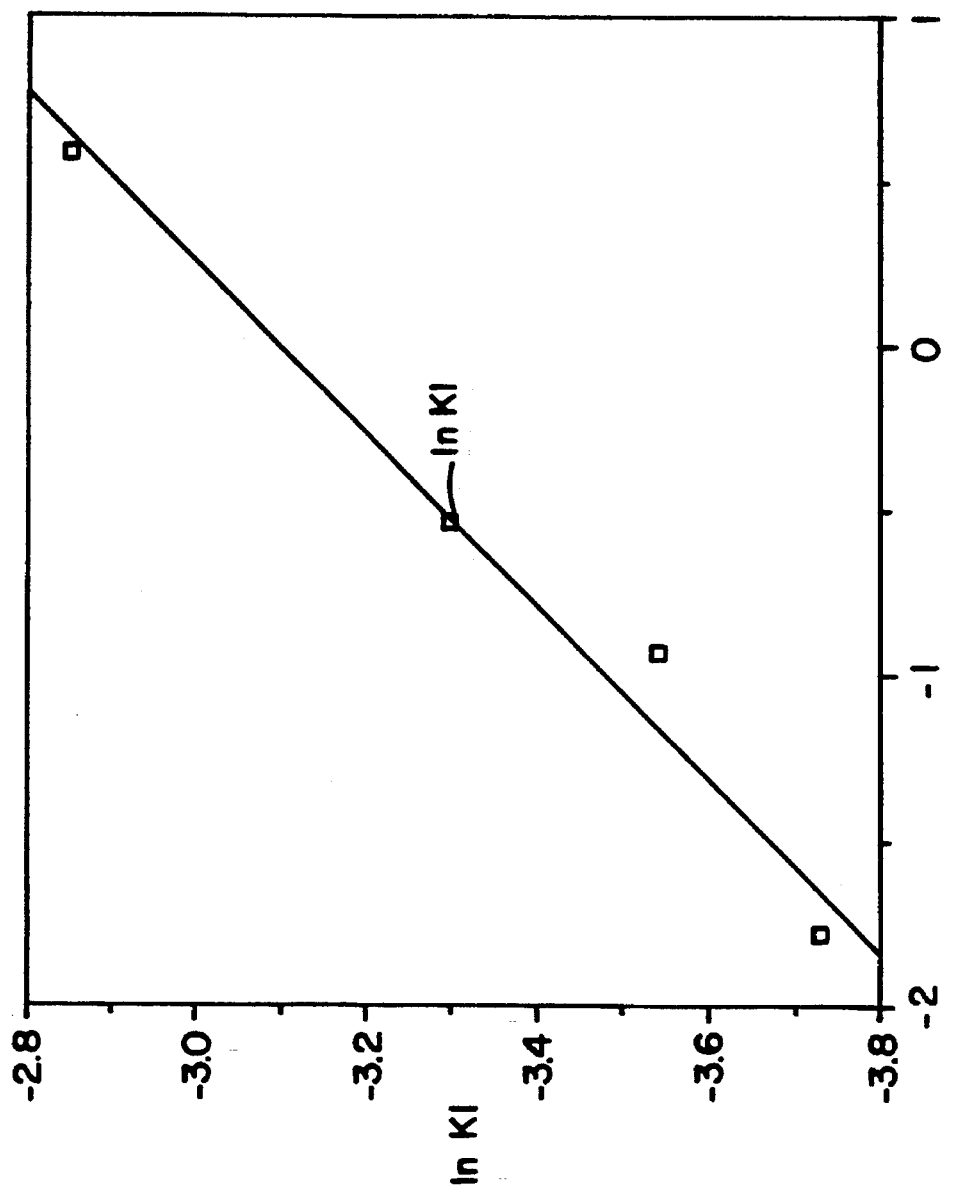

PROCESS FOR THE PRODUCTION OF 1,2-BIS (ACYLOXYLATES)

TECHNICAL FIELD

This invention relates to processes for acylation of epoxides with carboxylic anhydrides to produce 1,2-bis(acyloxyates). More particularly, this invention relates to catalysts for such processes.

BACKGROUND OF THE INVENTION 1,2-Bis(acyloxyates) are useful intermediates for organic synthesis. For example, 3,4-diacetoxy-1-butene is used in the production of vitamin A acetate, Paust, J., Pure and Appl. Chem., 63, 45 (1991). The 1,2-bis(acyloxylates) are the bis-esters of 1,2-dihydroxy compounds, or, alternatively, 1,2-diol dicarboxylates. The general formula for such compounds is shown in structure (I).

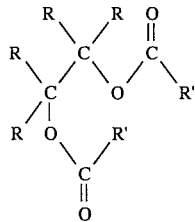

The preparation of 1,2-bis(acyloxylates) may be by acetylation of epoxides with acetic anhydride in the presence of various forms or combinations of amine catalysts. For example, a study by Shvets and Al-Wahib discloses that 1,2-diacetoxyethane can be prepared from ethylene oxide with acetic anhydride in the presence of pyridine and that the reaction proceeds by the intermediacy of N-(β-acetoxyethyl)pyridinium acetate. The reaction produces yields ranging from 45 to 93.5 percent. The yields decrease with increasing pyridine concentration at 0.05 to 1.00 M. Shvets, V. F. and Al-Wahib, Wahib, I., Kinet. Katal., 16(3), 785–8 (1975).

In another study by Shvets and Al-Wahib the nucleophilic catalysis of ethylene oxide is disclosed. The reaction of ethylene oxide with acetic anhydride is catalyzed by $(CH_3CH_2)_4N^{+}X^{-}$ (X=Cl, Br, I) and proceeds by attack of the halide anion on ethylene oxide to form the 2-haloethyl acetate and $(CH_3CH_2)_4N^{+}OAc^{-}$. The latter product continues to catalyze the reaction of ethylene oxide with acetic anhydride and also reacts with the 2-haloethyl acetate so that both processes lead to 1,2-diacetoxyethane. Product yields are typically low when using tetraalkylammonium halides. Shvets, V. F. and Al-Wahib, Wahib, I., Kinet. Katal., 16(2), 425–30 (1975).

As taught by Swindell, the nucleophilic catalysis of an epoxycyclooctane derivative with acetic anhydride catalyzed by 1,8-diazabicyclo[5.4.0]undec-7-ene (DBU) and LiCl in tetrahydrofuran produces the corresponding 1,2-bis(acyloxyate) at a 70 percent yield, Swindell, C. S. and Patel, B. P., J. Org. Chem., 55, 3 (1990). Fraser-Reid discloses that the reaction of epoxypyranosides with acetic anhydride catalyzed by $(CH_3CH_2CH_2CH_2)_4N^{+}OAc^{-}$ opens the epoxy ring to prepare the corresponding 1,2-bis(acyloxyate), Fraser-Reid, B. and Rahman, Md. A., J. Amer. Chem. Soc., 107, 5576 (1985).

Tetraalkylammonium acetates are produced by alkylation of a tertiary amine to form a quaternary ammonium salt in which the counterion is exchanged for acetate. Generally, this process requires isolation or purification of the intermediates. Thus, these types of catalysts are difficult to produce and costly.

The acid catalyzed ring opening of epoxides in the presence of acetic anhydride is also well known. For example, the acetylation of 3,4-epoxy-1-butene in the presence of acetic anhydride produces 3,4-diacetoxy-1-butene as disclosed by Evans, R. M., Fraser, J. B. and Owen, L. N., J. Chem Soc., 248 (1949). A 70 percent yield is obtained when using hydrochloric acid as the catalyst, while only a 39 percent yield is obtained using anhydrous zinc chloride as the catalyst. Another example of a Lewis acid catalyzed ring opening of an epoxide is disclosed by Ali, S. and Bittman, R., J. Org. Chem., 53, 5547, (1988) which describes the diacylation of glycidyl tosylate in the presence of boron trifluoride etherate with a 76 percent yield. These Lewis acid catalyzed acylations give reasonable yields. However, in practice Lewis acid catalysts do not give good process economics on large scale due to catalyst costs and the need to use expensive, corrosion-resistant materials of construction.

U.S. Pat. No. 5,189,199 to Godleski discloses the addition of oxygen nucleophiles to 3,4-epoxy-1-butene catalyzed by ligated Pd(O) to prepare 1,4-disubstituted-2-butenes. However, applying this process for the production of 3,4-diacetoxy-1-butene using acetic anhydride requires additional separation because it predominately produces 1,4-diacetoxy-2-butene. Its application is limited in scope since the substrate must be an epoxide in direct conjugation with a carbon-carbon double bond.

Other processes are commonly used to prepare 1,2-bis(acyloxyates) such as the acetylation of 1,2-diols with acetic anhydride or acetyl chloride. However, when using acetic anhydride, acetic acid is co-produced and must be removed or recycled in the process. With acetyl chloride, an excess of an organic base is generally needed to remove the corrosive hydrochloric acid that is co-produced in the process. In most cases, 1,2-bis(acyloxyates) are prepared from epoxides by acid catalyzed hydrolysis of epoxides to form the corresponding 1,2-dihydroxy derivative followed by acylation of the hydroxyl groups with an equivalent amount of carboxylic anhydride and organic base, such as pyridine or 4-(N,N-dimethylamino)pyridine. This overall process requires two chemical steps and isolation of intermediates.

Thus, there exists a need whereby 1,2-bis(acyloxyates) may be produced from epoxides in a single step process with increased rates of reaction and higher selectivities using relatively inexpensive catalysts, without the need to use corrosion resistant equipment, without the added costs of separating co-products and recovering by-products of the process and without the waste associated with the loss of catalysts. Accordingly, it is to the provision of such improved processes for the preparation of 1,2-bis(acyloxyates) that the present invention is primarily directed.

SUMMARY OF THE INVENTION

A process for the preparation of a 1,2-bis(acyloxyate) comprises acylation of an epoxide with a carboxylic anhydride in the presence of a catalytic composition containing a tertiary amine catalyst and a carboxylic acid co-catalyst. Preferably, the carboxylic acid is a conjugate acid of the carboxylic anhydride. The carboxylic acid in conjunction with the tertiary amine significantly increase the rate of reaction. The catalytic composition may be prepared prior to acylation or in situ providing application versatility.

BRIEF DESCRIPTION OF THE FIGURE

FIG. 1 is a graph of the natural logarithm (ln) of the first order rate constant versus the ln of the acetic acid concentration in the bis-acetylation of 3,4-epoxy-1-butene with acetic anhydride showing the dependence of the acetic acid concentration charged to the reactor in Example 3 and 9–11.

DETAILED DESCRIPTION OF THE INVENTION

In the preparation of 1,2-bis(acyloxyates) by the catalytic acylation of epoxides with carboxylic anhydrides, the use of catalytic compositions of tertiary amines with carboxylic acids has now been discovered to provide an improved process which increases the rates of reaction with minimal processing concerns. The catalytic species are believed to be tertiary ammonium carboxylate salts formed by the combination of the tertiary amines and the carboxylic acids either in a separate step or in situ. In the conversion of the epoxides to the 1,2-bis(acyloxyates), the epoxide rings are believed to be cleaved with the carboxylates of the catalytic species forming incipient alkoxides. The incipient alkoxides are concomitantly acylated by the carboxylates of the carboxylic anhydrides thereby producing 1,2-bis(acyloxyates).

The substituted 1,2-bis(acyloxyates) produced in accordance with the present invention have the formulas:

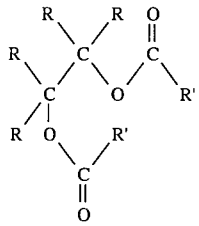

(I)

wherein the R and R' substituents are defined below with respect to the epoxide and carboxylic anhydride reactants, respectively.

The substituted epoxide reactants contain from 2 to about 20 carbon atoms, preferably from 3 to 8 carbon atoms. Examples of the substituted epoxide reactants include compounds having the structural formula:

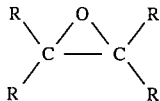

(II)

wherein each R is independently selected from hydrogen, alkyl or alkenyl of up to about 8 carbon atoms, carbocyclic, aryl or heterocyclic aryl of about 5 to 10 carbon atoms or any two R substituents collectively may represent an alkyl or alkenyl forming a ring, e.g., alkyl containing in the main chain 4 to about 6 carbon atoms. The preferred epoxide reactants comprise compounds of formula (II) wherein the R substituents individually represent hydrogen, lower alkyl of up to about 4 carbon atoms, or collectively represent a straight or branched chain alkyl or alkenyl of 2 to about 8 carbon atoms, especially compounds of formula (II) wherein 2 or more of the R groups represent hydrogen. Exemplary compounds contemplated for use in the practice of the present invention include 1,2-epoxybutane, 2,3-epoxybutane, 3,4-epoxy-1-butene, ethylene oxide, propylene oxide, styrene oxide, cyclohexene oxide, and the like. The epoxide reactant of primary interest is 3,4-epoxy-1-butene.

The preferred carboxylic anhydride reactants comprise compounds of formula $(R'CO)_2O$ wherein R' is independently selected from alkyl or alkenyl of up to about 15 carbon atoms or carbocyclic, aryl or heterocyclic aryl of about 5 to 10 carbon atoms. The carboxylic anhydrides are preferably reacted in an amount of at least 1 molar equivalent of the carboxylic anhydride to the epoxide. In excess amounts the carboxylic anhydrides act not only as reactants, but also as solvents.

The tertiary amine components of the catalytic compositions having the formula $R''_3N$ contain from about 3 to about 36 carbon atoms. The tertiary amines are preferably linear chain or non-aromatic cyclic amines and contain R" substituents independently selected from alkyl of up to about 12 carbon atoms or aryl or carbocyclic of about 5 to 15 carbon atoms. Exemplary compounds contemplated for use in the practice of the present invention include triethylamine, tributylamine, diisopropylethylamine, N,N-dimethylaniline, 4-methylmorpholine, 1-methylpyrrolidine, 1-methylpiperidine, 1,8-diazabicyclo[5.4.0]undec-7-ene, 1,4-diazabicyclo[2.2.2]octane and the like. The use of tertiary amines with low boiling points, especially triethylamine, allow the 1,2-bis(acyloxyates) to be readily separated from the catalysts since the tertiary amines can be distilled away from the products and recycled. The tertiary amines may also be supported in the form of resins or other solid supports.

Relative to the total amounts of tertiary amines and epoxides in the reactions, the tertiary amines are present in amounts ranging from about 0.1 to 40 mole percent and the epoxides are present in amounts ranging from about 99.9 to 60 mole percent. Preferably, the tertiary amines are present in amounts ranging from about 1 to 10 mole percent and the epoxides are present in amounts ranging from about 99 to 90 mole percent.

The carboxylic acid components of the catalytic compositions preferably contain from about 2 to 16 carbon atoms. More preferably, the carboxylic acids are conjugate acids of the carboxylic anhydrides. Thus, the carboxylic anhydride conjugate carboxylic acids having the formula R'COOH comprise R' substituents as defined above for the carboxylic anhydrides.

The catalytic compositions comprise the tertiary amines present in amounts ranging from about 0.1 to 50 mole percent and the carboxylic acids present in amounts ranging from about 99.9 to 50 mole percent, based on a total amount of tertiary amine and carboxylic acid. Preferably the tertiary amines are present in amounts ranging from about 1 to 15 mole percent and the carboxylic acids are present in amounts ranging from about 99 to 85 mole percent.

The tertiary amines act as catalysts by themselves and catalyze the reactions in the absence of the carboxylic acids. The carboxylic acids, however, do not function to catalyze the reactions in the absence of the tertiary amines. Rather, the carboxylic acids act as co-catalysts with the tertiary amines to increase the rates of reaction beyond that which either catalyst component alone would produce. In the case of disubstituted epoxides, the addition of the conjugate carboxylic acids significantly increases the reaction rates, as well as the degree of conversion. With terminal epoxides, the dependence on the carboxylic acid concentrations has been observed to give reaction orders of less than 1 and to enhance the selectivity.

The use of the conjugate carboxylic acids in excess relative to the tertiary amines provides an improvement to the process that would otherwise be unexpected. The carboxylic acids neutralize the tertiary amines forming the tertiary ammonium carboxylates at equivalent amounts. Thus, any excess carboxylic acid would be expected to react the same as if the carboxylic acid was the sole catalyst. Such is shown in Example 1 wherein the use of acetic acid as the sole catalyst results in a very slow reaction rate with low yield and selectivity. However, in the presence of tertiary ammonium carboxylates the addition of excess carboxylic acid unexpectedly increases the rate of reaction and produces higher yields and selectivity as shown in Example 9–11.

The significance of using the conjugate carboxylic acids is demonstrated in the conjugated epoxyalkene system of 3,4-epoxy-1-butene by the regioselective addition process of acetic anhydride in the presence of a tertiary ammonium acetate to prepare 3,4-diacetoxy-1-butene, a key intermediate in the manufacture of Vitamin A Acetate. Preferably, the tertiary ammonium acetate is triethylammonium acetate. Such acetylations of 3,4-epoxy-1-butene conducted under moderate temperatures of 50° to 200° C. at atmospheric pressure or under moderate pressure of an inert gas, such as nitrogen, give 88 to 94 mole percent 3,4-diacetoxy-1-butene and 1 to 5 mole percent 1,4-diacetoxy-2-butene.

As compared to pyridine or tetraalkylammonium acetates of the prior art, the tertiary ammonium acetates differ significantly in their chemical reactivity. The active catalytic species of the present invention are salt complexes of tertiary amines and carboxylic acids. The active species is created when the carboxylic acid protonates the basic amine function rendering the tertiary amine non-nucleophilic. Evidence supporting the involvement of the active species is the lack of reaction between the epoxides and tertiary amines in the absence of the carboxylic anhydrides and carboxylic acids. The epoxides are relatively stable to most carboxylic acids and carboxylic anhydrides in the absence of strong acids such as hydrochloric acid or sulfuric acid. The ammonium carboxylate anion of the tertiary ammonium carboxylates functions as a soluble form of nucleophilic carboxylate ion which initiates the cleavage of epoxides.

The use of the catalytic composition of the present invention also provides advantages over the prior art catalysts. A wide variety of carboxylic anhydrides and carboxylic acids may be used with tertiary amines to form a variety of acyloxy functional groups without multi-step preparation as is required for tetraalkylammonium carboxylates. The lower chain tertiary ammonium carboxylates, such as triethylammonium acetate, may also be recovered from the reaction mixture since this activated complex has a reasonably low boiling point. The tetraalkylammonium carboxylates, however, are non-volatile salts which decompose upon heating. Thus, the catalytic compositions of the present invention are more convenient to use and offer a significant cost advantage over the prior art.

The acylation conditions of temperature and pressure may vary depending on the reactants and catalysts employed. The acylation is generally conducted from about 50° to 200° C. The preferred temperature of operation is in the range of 100° to 125° C. The process may be carried out under atmospheric pressure or under moderate pressures of 50 to 250 psig (4.6 to 35.5 bar) which is advantageous when low boiling catalysts or reactants are employed. As noted above, the optimum combination of temperature and pressure depends on other process variables but can be readily ascertained by those skilled in the art.

The process of this invention optionally may be carried out in the presence of an inert, organic solvent. Examples of such solvents include aliphatic and aromatic hydrocarbons such as cyclohexane, heptane, toluene, xylene and mixed xylene isomers, ethers such as tetrahydrofuran, and amides such as N,N-dimethyl formamide and N-methyl-2-pyrrolidone. The preferred solvent system is the carboxylic anhydride that is used both as a solvent and reactant. The carboxylic anhydride is generally present in amounts of 1.0 molar equivalent to a large molar excess of anhydride relative to epoxide.

The process may be carried out in a batch, semi-continuous or continuous mode of operation. For example, batch operation may comprise agitating a tertiary amine, acetic acid, 3,4-epoxy-1-butene and acetic anhydride in a pressure vessel for a time sufficient to acylate essentially all of the 3,4-epoxy-1-butene to 3,4-diacetoxy-1-butene. The catalyst being a tertiary amine and conjugate carboxylic acid may be separated from the acylated mixture by washing with water and the components of the organic phase separated by distillation or preferably by fractional distillation of the reaction mixture.

The process provided by the present invention is further illustrated by the following examples which are intended to be exemplary of the invention. Gas chromatographic (GC) analyses were performed on a Hewlett-Packard 5890A gas chromatograph with a 30 meter, DB-5, 0.5 mm inside-diameter, capillary column with a 1.2 micron film thickness. Diglyme was used as an internal standard to reference composition percentages. The temperature program was 35° C. at 5 minutes, 20° C. increase per minute to 240° C., and hold 14.75 minutes. The identities of the products obtained were confirmed by nuclear magnetic spectrometry and gas chromatography-mass spectrometry. $^1$H NMR were recorded on a Gemini 300 MHz spectrometer and $^{13}$C NMR were recorded at 75 MHz.

EXAMPLE 1

A 300-mL autoclave was charged with 40 mL (0.50 mol) of 3,4-epoxy-1-butene, 67.3 g (0.66 mol) acetic anhydride, 5.82 g (0.097 mol) of acetic acid and 4.2 mL of diglyme. The autoclave was purged with nitrogen twice, then the vessel was pressurized to 8 bars (100 psig) with nitrogen. The agitator was started and an initial sample was taken. The mixture was heated to 125° C. During the course of 2.5 hrs, samples were taken every 15 min for analysis by GC. GC analysis of the crude mixture after 2.5 hrs revealed 11% yield of 3,4-diacetoxy-1-butene with a 13% selectivity, 21% 3,4-epoxy-1-butene and numerous high boiling components. The reaction was observed to be first order in 3,4-epoxy-1-butene with a first order rate constant (Kfirst) of 0.0025 min$^{-1}$ (Table A). This example illustrates low yield and selectivity in the absence of a tertiary amine and the inefficient catalysis of the reaction in the presence of the carboxylic acid alone.

EXAMPLE 2

A 300-mL autoclave was charged with 40 mL (0.50 mol) of 3,4-epoxy-1-butene, 63.2 g (0.62 mol) acetic anhydride, 4.06 g (0.041 mol) of triethylamine and 4.2 mL of diglyme. The autoclave was purged with nitrogen twice, then the vessel was pressurized to 8 bars (100 psig) with nitrogen. The agitator was started and an initial sample was taken. The mixture was heated to 125° C. During the course of 2.5 hrs, samples were taken every 15 min for analysis by GC. GC analysis of the crude mixture after 2.5 hrs revealed a 92% yield of 3,4-diacetoxy-1-butene with a 92% selectivity and 0.36% 3,4-epoxy-1-butene. The reaction was observed to be first order in 3,4-epoxy-1-butene with a first order rate constant of 0.037 min$^{-1}$ (Table A). This example demonstrates the catalytic effect of the tertiary amine alone.

EXAMPLE 3

A 300-mL autoclave was charged with 40 mL (0.50 mol) of 3,4-epoxy-1-butene, 62.2 g (0.61 mol) acetic anhydride, 1.8 g (0.018 mol) of triethylamine, 1.1 g (0.018 mol) acetic acid and 4.2 mL of diglyme. The autoclave was purged with nitrogen twice, then the vessel was pressurized to 8 bars (100 psig) with nitrogen. The agitator was started and an initial sample was taken. The mixture was heated to 125° C. During the course of 2 hrs, samples were taken every 15 min for analysis by GC. GC analysis of the crude mixture after 2 hrs revealed an 87% yield of 3,4 -diacetoxy-1-butene with an 89% selectivity and 1.8% 3,4-epoxy-1-butene. The reaction was observed to be first order in 3,4-epoxy-1-butene with a first order rate constant of 0.024 min$^{-1}$ (Table A). This example demonstrates the catalytic effect of the tertiary amine with acetic acid as the co-catalyst (Table B).

EXAMPLE 4

A 300-mL autoclave was charged with 40 mL (0.50 mol) of 3,4-epoxy-1-butene, 60.0 g (0.59 mol) acetic anhydride, 3.7 g (0.02 mol) of tributylamine, 0.72 g (0.012 mol) acetic acid and 4.2 mL of diglyme. The autoclave was purged with nitrogen twice, then the vessel was pressurized to 8 bars (100 psig) with nitrogen. The agitator was started and an initial sample was taken. The mixture was heated to 125° C. During the course of 2 hrs, samples were taken every 15 min for analysis by GC. GC analysis of the crude mixture after 2 hrs revealed a 79% yield of 3,4-diacetoxy-1-butene with a 90% selectivity and 12% 3,4-epoxy-1-butene. The reaction was observed to be first order in 3,4-epoxy-1-butene with a first order rate constant of 0.017 min$^{-1}$ (Table A). This example shows the catalytic effect of another tertiary amine with acetic acid as the co-catalyst.

EXAMPLE 5

A 100-mL autoclave was charged with 57.2 g (0.44 mol) propionic anhydride, 1.62 g (0.016 mol) of triethylamine and 3.44 g of diglyme. The autoclave was purged with helium twice, then the vessel was pressurized to 6.2 bars (75 psig) with helium followed by agitation. The reaction mixture was heated to 125° C., then 31.35 mL (0.40 mol) of 3,4-epoxy-1-butene was introduced to the reactor via syringe pump over 10 seconds. A first sample was taken at 1 min, then sequential samples were obtained every 15 min during the course of 2 hrs for analysis by GC. GC analysis of the crude mixture after 2 hrs revealed an 84% yield of 3,4-dipropionyloxy-1-butene with a 94% selectivity and 11.2% 3,4-epoxy-1-butene. The reaction was observed to be first order in 3,4-epoxy-1-butene with a first order rate constant of 0.017 min$^{-1}$ (Table A). This example shows the use of another carboxylic anhydride with triethylamine and no carboxylic acid co-catalyst.

EXAMPLE 6

A 100-mL autoclave was charged with 57.2 g (0.44 mol) propionic anhydride, 1.62 g (0.016 mol) of triethylamine, 1.2 g (0.016 mol) of propionic acid and 3.44 g of diglyme. The autoclave was purged with helium twice, then the vessel was pressurized to 6.2 bars (75 psig) with helium followed by agitation. The reaction mixture was heated to 125° C., then 31.35 mL (0.40 mol) of 3,4-epoxy-1-butene was introduced to the reactor via syringe pump over 10 seconds. A first sample was taken at 1 min, then sequential samples were obtained every 15 min during the course of 2 hrs for analysis by GC. GC analysis of the crude mixture after 2 hrs revealed a 90% yield of 3,4-dipropionyloxy-1-butene with a 91% selectivity and 6% 3,4-epoxy-1-butene. The reaction was observed to be first order in 3,4-epoxy-1-butene with a first order rate constant of 0.017 min$^{-1}$ (Table A). This example shows the use of another carboxylic anhydride with its conjugate carboxylic acid.

EXAMPLE 7

A 300-mL, 3-necked flask fitted with a thermocouple, condenser and stopper was charged with 47.5 g (0.21 mol) benzoic anhydride, 16 mL (0.2 mol) 3,4-epoxy-1-butene and 1.4 mL (0.008 mol) of diisopropylethylamine. The flask was purged with nitrogen then heated to reflux. The reaction was discontinued after 1.5 hr when the temperature reached 160° C. GC analysis revealed a mixture of about 1% starting material, 10–15% monocarboxylates (confirmed by GC-MS), 4% 1,4-bis(acyloxate) and about 80% of the desired 1,2-bis(acyloxate). The reaction mixture was diluted with ether, washed with dilute HCl, washed twice with water, and then dried over Na$_2$SO$_4$. The ether was removed under vacuum, and the residue was distilled at 0.15 mm Hg. Three fractions were obtained with the last two fractions containing the 1,2-bis(acyloxyates) for a combined yield of 62%. Fraction 2 results were 36.5 g of 95% 3,4-dibenzoyloxy-1-butene and 5% monocarboxylates with bp of 155°–165° C. Fraction 3 results were 21.5 g of 93% 3,4-dibenzoyloxy-1-butene and 7% 1,4-dibenzoyloxy-2-butene with bp of 165°–170° C. $^1$H NMR (CDCl$_3$) δ8.08 (dd, J=0.7, 6.3, 4 H), 7.45 (m, 6 H), 5.98 (m, 2 H), 5.51 (d, J=17 Hz, 1 H), 5.35 (d, J=10.4 Hz, 1 H) 4.56 (m, 2 H); $^{13}$C NMR (CDCl$_3$) δ170.3, 73.6, 30.0, 23.3, 21.0. This example demonstrates the use of a very reactive carboxylic anhydride with a hindered tertiary amine (Table A).

EXAMPLE 8

A 300-mL, 3-necked flask fitted with a thermocouple, condenser and stopper was charged with 47.5 g (0.21 mol) benzoic anhydride, 0.49 g (0.004 mol) benzoic acid, 16 mL (0.2 mol) 3,4-epoxy-1-butene and 1.4 mL (0.008 mol) of diisopropylethylamine. The flask was purged with nitrogen then heated to reflux. The reaction was discontinued after 3 hrs of maintaining the temperature at 130° C. GC analysis revealed a mixture of about 1% starting material, 10% monocarboxylates, 2% 1,4-bis(acyloxate) and about 87% of the desired 1,2-bis(acyloxate). This example shows the use of a very reactive carboxylic anhydride and a hindered tertiary amine with the conjugate carboxylic acid (Table A).

EXAMPLE 9

A 100-mL autoclave was charged with 45.25 g (0.44 mol) acetic anhydride, 1.62 g (0.016 mol) of triethylamine, 1.94 g (0.032 mol) acetic acid and 3.44 g of diglyme. The autoclave was purged with helium twice, then the vessel was pressurized to 6.2 bars (75 psig) with helium followed by agitation. The reaction mixture was heated to 125° C. Then 31.35 mL (0.40 mol) of 3,4-epoxy-1-butene was introduced to the reactor via syringe pump over 10 seconds. A first sample was taken at 1 min, then sequential samples were obtained every 15 min during the course of 2.25 hrs for analysis by GC. GC analysis of the crude mixture after 2.25 hrs revealed a 93% yield of 3,4-diacetoxy-1-butene with a 95% selectivity and 1.9% 3,4-epoxy-1-butene. The reaction was observed to be first order in 3,4-epoxy-1-butene with a first order rate constant of 0.029 min$^{-1}$ (Table A). This example demonstrates the catalytic effect of a tertiary amine with two molar equivalents of acetic acid as a co-catalyst (Table B).

EXAMPLE 10

A 300-mL autoclave was charged with 40 mL (0.50 mol) of 3,4-epoxy-1-butene, 56.2 g (0.55 mol) acetic anhydride, 2.0 g (0.02 mol) of triethylamine, 3.6 g (0.06 mol) acetic acid and 4.2 mL of diglyme. The autoclave was purged with nitrogen twice, then the vessel was pressurized to 8 bars (100 psig) with nitrogen. The agitator was started and an initial sample was taken. Then the mixture was heated to 125° C. During the course of 2.5 hrs, samples were obtained every 15 min for analysis by GC. GC analysis of the crude mixture after 2.5 hrs revealed a 96% yield of 3,4-diacetoxy-1-butene and 1.4% 3,4-epoxy-1-butene. The reaction was observed to be first order in 3,4-epoxy-1-butene with a first order rate constant of 0.037 min$^{-1}$ (Table A). This example demonstrates the catalytic effect of a tertiary amine with three molar equivalents of acetic acid (Table B).

EXAMPLE 11

A 100-mL autoclave was charged with 45.25 g (0.44 mol) acetic anhydride, 1.62 g (0.016 mol) of triethylamine, 9.6 g (0.16 mol) acetic acid and 3.44 g of diglyme. The autoclave was purged with helium twice, then the vessel was pressurized to 6.2 bars (75 psig) with helium followed by agitation. The reaction mixture was heated to 125° C., then 31.35 mL (0.40 mol) of 3,4-epoxy-1-butene was introduced to the reactor via syringe pump over 10 seconds. A first sample was obtained at 1 min, then sequential samples were obtained every 15 min during the course of 2.25 hrs for analysis by GC. GC analysis of the crude mixture after 2.25 hrs revealed 94% 3,4-diacetoxy-1-butene with no 3,4-epoxy-1-butene remaining. The reaction was observed to be first order in 3,4-epoxy-1-butene with a first order rate constant of 0.058 min$^{-1}$ (Table A). This example shows the catalytic effect of a tertiary amine with ten molar equivalents of acetic acid (Table B).

Kinetic Effect of Acetic Acid Co-catalyst

The effect of acetic acid co-catalyst in the rate of addition of acetic anhydride to 3,4-epoxy-1-butene to form 3,4-diacetoxy-1-butene was demonstrated in Examples 3, 9–11 and is set forth in Table B. The dependence of the acetic acid concentration charged to the reactor was correlated with the rate constant by plotting the natural logarithm (ln) of the first order rate constant versus ln of the acetic acid concentration as shown in FIG. 1. The dependence on acetic acid concentration is expressed as the slope of the line shown in FIG. 1. The slope is 0.38 indicating a dependence that is less than first order. This reaction order suggests that the acid catalyst plays a significant role in a complex mechanism and may be involved in more than one step of the mechanism. A linear correlation of 0.977 indicates a very good correlation in the range of one molar equivalent of acetic acid to 10 molar equivalents relative to triethylamine. The acetic acid is observed to enhance the rate and selectivity, but is not first order in acetic acid.

TABLE B

| Example | Kfirst (min-1) | AcOH Molarity | ln Kfirst | ln AcOH Molarity |
|---|---|---|---|---|
| 3 | 0.024 | 0.171 | −3.730 | −1.766 |
| 9 | 0.029 | 0.396 | −3.540 | −0.926 |
| 10 | 0.037 | 0.586 | −3.297 | −0.534 |
| 11 | 0.058 | 1.81 | −2.847 | 0.593 |

EXAMPLE 12

A 300-mL, 3-necked flask fitted with a thermocouple, condenser and stopper was charged with 181 mL (1.6 mol) acetic anhydride, 62.7 mL (0.8 mol) 3,4-epoxy-1-butene, 7.2 mL (0.04 mol) of diisopropylethylamine and 2.4 g (0.04 mol) of acetic acid. The flask was purged with nitrogen then heated to reflux. The reaction was complete after 48 hrs. GC analysis revealed only the desired 3,4-diacetoxy-1-butene. The reaction mixture was washed with dilute HCl and water, then dried over Na$_2$SO$_4$. Distillation at 2.0 mm Hg (bp 66°–68° C.) gave 101.4 g for a combined yield of 74%. $^1$H NMR (CDCl$_3$) δ5.78 (m, 1 H), 5.46 (m, 1 H), 5.33 (dd, J=1.1, 17.3 Hz, 1 H), 5.25 (dd, J=1.1, 10.3 Hz, 1 H), 4.22 (dd, J=3.7, 12.0 Hz, 1 H), 4.07 (dd, J=7.1, 12.0 Hz, 1 H), 2.07 (s, 3 H), 2.04 (s, 3 H); $^{13}$C NMR (CDCl$_3$) δ170.4, 169.7, 132.1, 118.5, 71.8, 64.5, 20.8, 20.5. This example shows that even when using acetic acid as a co-catalyst a hindered tertiary amine is slow to react (Table C).

TABLE A

| Ex. | RXN Time (Min.) | Moles of 3,4-Epoxy-1 Butene | Moles of Amine | Moles of Acid | % 3,4-Diacyloxy-1-Butene | % 1,4-Diacyloxy-1-Butene | Kfirst (min-1) |
|---|---|---|---|---|---|---|---|
| 1 | 150 | 0.5 | 0.00 | 0.097 | 11 | 1 | 0.0025 |
| 2 | 150 | 0.5 | 0.041 | 0 | 92 | 0.2 | 0.037 |
| 3 | 120 | 0.5 | 0.02 | 0.02 | 87 | 1 | 0.024 |
| 4 | 120 | 0.5 | 0.02 | 0.012 | 79 | 0 | 0.017 |
| 5 | 120 | 0.4 | 0.016 | 0 | 84 | 5 | 0.017 |
| 6 | 120 | 0.4 | 0.016 | 0.016 | 90 | 3 | 0.023 |
| 7 | 90 | 0.2 | 0.008 | 0 | 80 | 4 | — |
| 8 | 180 | 0.2 | 0.008 | 0.004 | 87 | 1 | — |
| 9 | 135 | 0.4 | 0.016 | 0.032 | 93 | 1.4 | 0.029 |
| 10 | 150 | 0.5 | 0.02 | 0.06 | 96 | 1 | 0.037 |
| 11 | 135 | 0.4 | 0.016 | 0.16 | 94 | 4 | 0.058 |

EXAMPLE 13

A 300-mL autoclave was charged with 35 mL (0.50 mol) of propylene oxide, 95 mL (1.01 mol) acetic anhydride and 2.8 mL (0.02 mol) of triethylamine. The autoclave was purged with nitrogen twice, then the vessel was pressurized to 8 bars (100 psig) with nitrogen followed by agitation. The reaction was conducted for 4 hrs at 120° C. After 4 hrs, GC analysis revealed complete conversion to 1,2-diacetoxypropane with greater than 99% selectivity. The reaction mixture was washed three times with dilute HCl then distilled through a short Vigreux column at 4 mm Hg, bp 75°–77° C. A total of 50.3 g was obtained with a combined yield of 63%.

¹H NMR (CDCl₃) δ5.04 (m, 1 H) , 4.09 (dd, J=6.6, 11.8 Hz, 1 H), 2.00 (s, 3 H), 1.98 (s, 3 H), 1.17 (d, J=6.5 Hz, 3 H); ¹³C NMR (CDCl₃) δ170.6, 170.3, 68.1, 65.9, 21.0, 20.6, 16.3. This example shows the production of a 1,2-bis(acyloxyate) from another type of an epoxide (Table C).

EXAMPLE 14

A 300-mL autoclave was charged with 43 mL (0.50 mol) of 1,2-butylene oxide, 95 mL (1.01 mol) acetic anhydride and 2.8 mL (0.02 mol) of triethylamine. The autoclave was purged with nitrogen twice, then the vessel was pressurized to 8 bars (100 psig) with nitrogen followed by agitation. The reaction was conducted for 4 hrs at 120° C. After 4 hrs, GC analysis revealed complete conversion to 1,2-diacetoxybutane with greater than 99% selectivity. The reaction mixture was washed two times with dilute HCl then distilled through a short Vigreux column at 3 mm Hg, bp 83°–85° C. A total of 72.9 g was obtained with a combined yield of 84%. ¹H NMR (CDCl₃) 64.95 (m, 1 H), 4.18 (dd, J=3.4, 11.9 Hz, 1 H), 3.98 (dd, J=6.6, 11.9 Hz, 1 H), 2.00 (s, 3 H), 1.99 (S, 3 H), 1.55 (q, J=7.5 HZ, 2 H), o.aa (t, J=7.5 Hz, 3 H); ¹³C NMR (CDCl₃) δ170.6, 170.4, 72.6, 64.6, 23.6, 20.8, 20.6, 9.3. This example demonstrates the production of a 1,2-bis(acyloxyate) from another type of epoxide without an acid co-catalyst (Table C).

EXAMPLE 15

A 300-mL, 3-necked flask fitted with a thermocouple, condenser and stopper was charged with 49.5 mL (0.53 mol) acetic anhydride, 43 mL (0.5 mol) 1,2-butylene oxide, 2.8 mL (0.04 mol) of triethylamine and 2.2 mL (0.02 mol) of acetic acid. The flask was purged with nitrogen then heated to reflux. The reaction was complete after 5 hrs. GC analysis revealed the desired 1,2-diacetoxybutane plus another side-product. The reaction mixture was washed with dilute HCl and water, then dried over Na₂SO₄. The side-product was no longer present after the aqueous workup. Distillation at 3.5 mm Hg (bp 84°–85° C.) gave 74 g for a combined yield of 85%. This example shows the production of a 1,2-bis(acyloxyate) from another epoxide using acetic acid as a co-catalyst (Table C).

EXAMPLE 16

A 300-mL, 3-necked flask fitted with a thermocouple, condenser and stopper was charged with 76 mL (0.8 mol) acetic anhydride, 45.5 mL (0.4 mol) stryrene oxide and 2.25 mL (0.016 mol) of triethylamine. The flask was purged with nitrogen then heated to reflux. The reaction was complete after 2 hrs. GC analysis of the crude reaction product revealed the desired diacetate in 95% assay. The reaction mixture was washed with dilute HCl and water, then dried over Na₂SO₄. Distillation of the product at 2.2 mm Hg (bp 110°–112° C.) gave 74.5 g of 1,2-diacetoxy-1-phenylethane for a combined yield of 84%. ¹H NMR (CDCl₃) δ7.34 (m, 5 H) , 6.03 (dd, J=3.5, 7.7 Hz, 1 H) , 4.33 (m, 2 H), 2.12 (s, 3 H), 2.06 (s, 3 H); ¹³C NMR (CDCl₃) δ170.5, 169.9, 136.4, 128.6, 128.5, 126.6, 73.2, 66.0, 21.0, 20.7. This example shows the production of a 1,2-bis(acyloxyate) from another epoxide without a co-catalyst (Table C).

EXAMPLE 17

A 300-mL, 3-necked flask fitted with a thermocouple, condenser and stopper was charged with 76 mL (0.53 mol) acetic arthydride, 45.5 mL (0.4 mol) styrene oxide, 2.25 mL (0.016 mol) of triethylamine and 0.9 mL (0.016 mol) of acetic acid. The flask was purged with nitrogen then heated to reflux for 1.5 hrs. The reaction mixture was washed with dilute HCl and water, then dried over Na₂SO₄. Distillation of the product at 0.25 mm Hg (bp 100°–102° C.) gave 71.4 g of 1,2-diacetoxy-1-phenylethane with a yield of 80%. This example shows the production of a 1,2-bis(acyloxyate) from another epoxide with acetic acid as a co-catalyst (Table C).

EXAMPLE 18

A 25-mL round-bottomed flask was charged with 10 mL (0.052 mol) acetic anhydride, 5 g (0.1 mol) cyclohexene oxide and 0.14 mL (0.002 mol) of triethylamine. The flask was purged with nitrogen then heated to reflux. The reaction was monitored as a function of time by GC analysis. After 16 hrs, the reaction was only 50.6% complete in the absence of acetic acid co-catalyst. This example shows the production of a 1,2-bis(acyloxyate) from another epoxide and that the reaction is slow with a disubstituted epoxide in the absence of acetic acid co-catalyst (Table C).

EXAMPLE 19

A 300-mL, 3-necked flask fitted with a thermocouple, condenser and stopper was charged with 49 mL (0.52 mol) acetic anhydride, 25 g (0.26 mol) cyclohexene oxide, 1.4 mL (0.01 mol) of triethylamine and 0.6 mL (0.01 mol) of acetic acid. The flask was purged with nitrogen then heated to reflux for 16 hrs. The reaction mixture was washed with dilute HCl then distilled at 1.6 mm Hg (bp 99°–102° C.) to give 42 g of 1,2-diacetoxycyclohexane with a yield of 81%. ¹H NMR (CDCl₃) δ4.75 (m, 2 H), 2.01 (m, 2 H), 1.98 (s, 6 H), 1.69 (m, 2 H), 1.32 (brm, 4 H); ¹³C NMR (CDCl₃) δ170.3, 73.6, 30.0, 23.3, 21.0. This example shows the production of a 1,2-bis(acyloxyate) from a disubstituted epoxide with acetic acid as a co-catalyst which results in higher conversions as compared to without acetic acid (Table C).

TABLE C

| Ex. | RXN Time (Hrs.) | Epoxide | Anhydride | Amine | Acid | % Isolated Dicarboxylate Ester |
|---|---|---|---|---|---|---|
| 12 | 48 | 3,4-Epoxy-1-butene | Acetic | (i-Pr)2NEt | AcOH | 74 |
| 13 | 4 | Propylene oxide | Acetic | NEt3 | None | 63 |
| 14 | 4 | Butylene oxide | Acetic | NEt3 | None | 84 |
| 15 | 5 | Butylene oxide | Acetic | NEt3 | AcOH | 85 |

TABLE C-continued

| Ex. | RXN Time (Hrs.) | Epoxide | Anhydride | Amine | Acid | % Isolated Dicarboxylate Ester |
|---|---|---|---|---|---|---|
| 16 | 2 | Styrene oxide | Acetic | NEt3 | None | 84 |
| 17 | 1.5 | Styrene oxide | Acetic | NEt3 | AcOH | 80 |
| 18 | 16 | Cyclohexene oxide | Acetic | NEt3 | None | 51 (Unisolated) |
| 19 | 16 | Cyclohexene oxide | Acetic | NEt3 | AcOH | 81 |

As thus seen, the catalytic composition of the present invention produces 1,2-bis(acyloxyates) from the acylation of epoxides with carboxylic anhydrides with improved process results. The tertiary amine and carboxylic acid catalytic compositions are relatively inexpensive because preparation is minimal. The rates of reaction are increased and higher selectivity is obtained, thus reducing the need for extensive separation and by-product recovery equipment.

The invention has been described in detail with particular reference to preferred processes thereof, but it will be understood that variations and modifications can be effected within the spirit and scope of the invention.

What is claimed is:

1. A process for the preparation of a 1,2-bis(acyloxyate) which comprises reacting an epoxide with a carboxylic anhydride in the presence of a catalytic amount of a catalytic composition containing a tertiary amine and a carboxylic acid.

2. The process of claim 1 wherein said carboxylic acid is a conjugate acid of said carboxylic anhydride.

3. The process of claim 2 wherein said carboxylic anhydride having the formula $(R'CO)_2O$ and said conjugate acid having the formula $R'COOH$ contain R' substituents selected from a group consisting of alkyl or alkenyl of up to about 15 carbon atoms or carbocyclic, aryl or heterocyclic aryl of about 5 to 10 carbon atoms.

4. The process of claim 1 wherein said epoxide has the formula $(R_2C)_2O$ and contains R substituents independently selected from a group consisting of hydrogen, alkyl or alkenyl of up to about 8 carbon atoms, carbocyclic, aryl or heterocyclic aryl of about 5 to 10 carbon atoms or any two of said R substituents collectively representing alkyl or alkenyl forming a ring.

5. The process of claim 4 wherein said R substituents individually represent hydrogen, lower alkyl of up to about 4 carbon atoms, or straight or branched chain alkenyl of 2 to about 8 carbon atoms.

6. The process of claim 5 wherein two or more of said R substituents represent hydrogen.

7. The process of claim 1 wherein said tertiary amine contains from about 3 to 36 carbon atoms.

8. The process of claim 1 wherein said tertiary amine is a non-aromatic cyclic amine.

9. The process of claim 1 wherein said tertiary amine having the formula $R''_3N$ contains R" substituents independently selected from a group consisting of alkyl of up to about 12 carbon atoms or aryl or carbocyclic of about 5 to 10 carbon atoms.

10. The process of claim 1 wherein said tertiary amine is present in an amount ranging from about 0.1 to 40 mole percent and said epoxide is present in an amount ranging from about 99.9 to 60 mole percent, based on a total amount of said tertiary amine and said epoxide.

11. The process of claim 10 wherein said tertiary amine is present in an amount ranging from 1 to 10 mole percent and said epoxide is present in an amount ranging from about 99 to 90 mole percent.

12. The process of claim 1 wherein said tertiary amine is present in an amount ranging from about 0.1 to 50 mole percent and said carboxylic acid is present in an amount ranging from about 99.9 to 50 mole percent, based on a total amount of said tertiary amine and said carboxylic acid.

13. The process of claim 12 wherein said tertiary amine is present in an amount ranging from about 1 to 15 mole percent and said carboxylic acid is present in an amount ranging from about 99 to 85 mole percent.

14. The process of claim 1 wherein said carboxylic anhydride is reacted in an amount of at least 1 molar equivalent of said carboxylic anhydride to said epoxide.

15. The process of claim 1 wherein said catalytic composition is formed in situ by the addition of independent amounts of said tertiary amine and said carboxylic acid.

16. A process for the preparation of 3,4-diacetoxy-1-butene which comprises reacting 3,4-epoxy-1-butene with acetic anhydride in the presence of a catalytic amount of a catalytic composition of a tertiary ammonium acetate being formed from a tertiary amine having from about 3 to about 36 carbon atoms and acetic acid.

17. The process of claim 16 wherein said tertiary amine is triethylamine.

18. A process for the preparation of a 1,2-bis(acyloxyate) which comprises (a) preparing a catalytic composition of a tertiary amine and a carboxylic acid and (b) reacting an epoxide with a carboxylic anhydride in the presence of a catalytic amount of said catalytic composition, whereby the addition of the carboxylic acid to the tertiary amine increases the rate of reaction.

19. The process of claim 16 wherein said carboxylic acid is a conjugate acid of said carboxylic anhydride.

* * * * *